(12) United States Patent
Milner et al.

(10) Patent No.: US 11,490,923 B2
(45) Date of Patent: Nov. 8, 2022

(54) DEVICE WITH SHARP AND BLUNT REGIONS FOR REMOVING OCCLUSIONS

(71) Applicant: Cook Medical Technologies LLC, Bloomington, IN (US)

(72) Inventors: Keith Milner, West Lafayette, IN (US); Joshua Krieger, Topsfield, MA (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 715 days.

(21) Appl. No.: 16/239,655

(22) Filed: Jan. 4, 2019

(65) Prior Publication Data

US 2019/0209195 A1 Jul. 11, 2019

Related U.S. Application Data

(60) Provisional application No. 62/613,913, filed on Jan. 5, 2018.

(51) Int. Cl.
*A61B 17/3207* (2006.01)
*A61B 17/32* (2006.01)

(52) U.S. Cl.
CPC .. *A61B 17/3207* (2013.01); *A61B 17/320725* (2013.01); *A61B 17/320758* (2013.01); *A61B 2017/320044* (2013.01)

(58) Field of Classification Search
CPC ........ A61B 17/320758; A61B 17/3207; A61B 17/320708; A61B 17/320725; A61B 17/32075; A61B 17/32096; A61B 2017/320716; A61B 2017/320733; A61B 2017/320741; A61B 2017/320766; A61B 2017/320775; A61B 2017/320044
See application file for complete search history.

(56) References Cited

U.S. PATENT DOCUMENTS

| | | | |
|---|---|---|---|
| 3,952,747 A | 4/1976 | Kimmell, Jr. | |
| 5,030,201 A * | 7/1991 | Palestrant | A61B 17/320725 604/22 |
| 5,071,424 A * | 12/1991 | Reger | A61B 17/32075 606/159 |
| 5,112,345 A | 5/1992 | Farr et al. | |
| 5,154,724 A * | 10/1992 | Andrews | A61B 17/320725 604/22 |
| 5,156,610 A * | 10/1992 | Reger | A61B 17/32075 30/348 |
| 5,178,625 A * | 1/1993 | Groshong | A61B 17/32075 604/22 |

(Continued)

OTHER PUBLICATIONS

Extended European Search Report for 19 150 620.3 dated Jun. 6, 2019, 9 pgs.

*Primary Examiner* — Dianne Dornbusch
(74) *Attorney, Agent, or Firm* — Crowell & Moring LLP (57) ABSTRACT

Disclosed herein is a device for disrupting material in a body vessel and a method for making such a device. The device includes a plurality of arms disposed circumferentially about an axis. Each arm includes two blades; one sharper, and one blunter. The sharper blades are all oriented in the same direction, clockwise or counterclockwise, such that when the device is rotated in a first direction, the sharper blades engage the material, and in the other, the duller blades engage the material.

14 Claims, 5 Drawing Sheets

(56) References Cited

U.S. PATENT DOCUMENTS

| | | | |
|---|---|---|---|
| 5,192,291 A * | 3/1993 | Pannek, Jr. | A61B 17/320725 604/22 |
| 5,441,510 A | 8/1995 | Simpson et al. | |
| 5,507,760 A | 4/1996 | Wynne et al. | |
| 5,795,322 A | 8/1998 | Boudewijn | |
| 5,810,874 A | 9/1998 | Lefebvre | |
| 5,814,064 A | 9/1998 | Daniel et al. | |
| 5,885,258 A | 3/1999 | Sachdeva et al. | |
| 5,928,260 A | 7/1999 | Chin et al. | |
| 5,976,172 A | 11/1999 | Homsma et al. | |
| 6,096,053 A | 8/2000 | Bates | |
| 6,165,187 A * | 12/2000 | Reger | A61B 17/32075 606/159 |
| 6,355,051 B1 | 3/2002 | Sisskind et al. | |
| 6,562,058 B2 | 5/2003 | Seguin et al. | |
| 6,629,953 B1 | 10/2003 | Boyd | |
| 6,780,175 B1 | 8/2004 | Sachdeva et al. | |
| 6,893,450 B2 | 5/2005 | Foster | |
| 7,713,235 B2 | 5/2010 | Torrance et al. | |
| 8,361,094 B2 | 1/2013 | Danek et al. | |
| 8,696,695 B2 | 4/2014 | Patel et al. | |
| 9,345,508 B2 | 5/2016 | Hendrick | |
| 9,445,834 B2 | 9/2016 | Lee et al. | |
| 9,549,755 B2 | 1/2017 | Schneider et al. | |
| 2001/0031981 A1 | 10/2001 | Evans et al. | |
| 2005/0021071 A1 | 1/2005 | Konstantino et al. | |
| 2006/0276816 A1 * | 12/2006 | Eckman | A61B 17/320708 606/160 |
| 2008/0086157 A1 | 4/2008 | Stad et al. | |
| 2010/0125253 A1 | 5/2010 | Olson et al. | |
| 2010/0228280 A1 | 9/2010 | Groothuis et al. | |
| 2011/0184447 A1 * | 7/2011 | Leibowitz | A61B 17/320016 606/170 |
| 2012/0239064 A1 | 9/2012 | Cartier et al. | |
| 2014/0309672 A1 * | 10/2014 | Labropoulos | A61B 17/320758 606/159 |
| 2016/0199617 A1 * | 7/2016 | Pigott | A61B 17/320725 604/22 |
| 2016/0220269 A1 | 8/2016 | Labropoulos et al. | |

\* cited by examiner

DEVICE WITH SHARP AND BLUNT REGIONS FOR REMOVING OCCLUSIONS

BACKGROUND

The present application generally relates to medical devices. More particularly, the present application relates to a device for disrupting material within a body vessel, such as in a venous thrombectomy or atherectomy procedure.

A number of disease states can lead to the full or partial occlusion of the lumen of a vessel, such as atherosclerosis leading to the occlusion of an artery, or deep vein thrombosis, leading to occlusion of a vein. There are a number of minimally-invasive procedures and related devices that can be used to remove these occlusions, such as atherectomy and thrombectomy. A number of these devices rely on rotating elements to mechanically disrupt the occlusion, with the disrupted material being subsequently removed to restore patency to the vessel lumen.

Vascular occlusions are frequently heterogeneous in nature. Atherosclerotic plaques may contain regions with soft, fatty deposits, and other regions with heavy calcification. Venous thrombotic occlusions may have regions with acute, soft thrombus and with sub-acute cross-linked fibrotic regions. Currently available medical devices typically do not allow control of the cutting or disruptive ability of the system, other than by changing the speed at which the system rotates. A system that would allow the physician to more readily vary the disruptive power of the device in response to changing properties of the occlusion would facilitate removal while limiting damage to the underlying blood vessel, minimizing such undesired consequences as venous valve damage, perforation, endothelium denudation, and the like.

It has been a challenge to develop a rotary tool which is capable of processing material in a body vessel which includes both sharp and dull cutting surfaces.

SUMMARY

In one aspect, the present disclosure provides a medical device for disrupting material in a body vessel, the medical device comprising: a body comprising a first end and extending to a second end, the body comprising an inner surface and an outer surface opposite the inner surface, the body comprising a first tubular portion, a plurality of arms, and a second tubular portion, the plurality of arms being disposed between and connected to the first tubular portion and the second tubular portion, the first tubular portion comprising the first end and the body defining a longitudinal axis therethrough; the second tubular portion comprising the second end and disposed about the longitudinal axis, the second tubular portion being axially displaced from the first tubular portion; and each of the plurality of arms comprising: an outer face continuous with the outer surface, an inner face continuous with the inner surface, a first blade, and a second blade; each of the first blade and the second blade being disposed between the outer face and the inner face, the first blade being sharper than the second blade; and each of the plurality of arms being arranged such that each first blade is in the same relative orientation in a circumferential direction.

In another aspect, the present disclosure provides a medical device for disrupting material in a body vessel, the medical device comprising: a body comprising a first end and extending to a second end, the body comprising an inner surface and an outer surface opposite the inner surface, the body comprising a first tubular portion, a plurality of arms, and a second tubular portion, the plurality of arms being disposed between and connected to the first tubular portion and the second tubular portion, the first tubular portion comprising the first end and the body defining a longitudinal axis therethrough; the second tubular portion comprising the second end and disposed about the longitudinal axis, the second tubular portion being axially displaced from the first tubular portion; and each of the plurality of arms comprising: an outer face continuous with the outer surface, an inner face continuous with the inner surface, a first faceted blade, and a second blade; each of the first faceted blade and the second blade being disposed between the outer face and the inner face, the first blade being sharper than the second blade; and each of the plurality of arms being arranged such that each first faceted blade is in the same relative orientation in a circumferential direction.

In a further aspect, the present disclosure provides a method of making a medical device for disrupting material in a body vessel, the method comprising: making a plurality of first cuts in a tubular body, the tubular body comprising an inner surface and an outer surface and extending from a first end to a second end defining a longitudinal axis therethrough, each first cut originating between the first end and the second end and terminating between the first end and the second end; making a plurality of second cuts in the tubular body offset from the first cut to define a plurality of arm region between each first cut and its corresponding second cut, each second cut originating between the first end and the second end and terminating between the first end and the second end; displacing a portion of each arm region outward radially to define a plurality of arms, each arm comprising a first blade defined by the first cut and having a first sharpness, and a second blade defined by the second cut and having a second sharpness different than the first sharpness, each of the plurality of arms being oriented such that each first blade is in the same relative orientation in a circumferential direction, wherein at least one of the first cuts and the second cuts are made in a plane which does not intersect the longitudinal axis.

Further objects, features and advantages of this system will become readily apparent to persons skilled in the art after a review of the following description, with reference to the drawings and claims that are appended to and form a part of this specification.

DETAILED DESCRIPTION

The drawings are purely schematic illustrations of various aspects of the device and method being described, and are not necessarily to scale, unless expressly stated.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part. When used in the context of a numerical value or range set forth, "about" or "substantially" means a variation of ±15%, or less, of the numerical value. For example, a value differing by ±15%, ±14%, ±10%, or ±5%, among others, would satisfy the definition of "about."

Figure 1A:
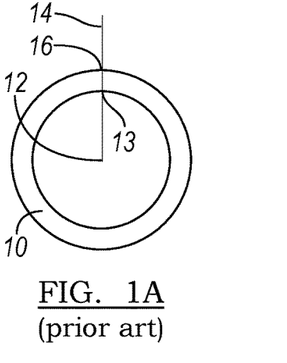
FIGS. 1A-1E are schematic views of cuts made to create a vascular treatment device constructed in accordance with a prior art method.
Figure 1B:
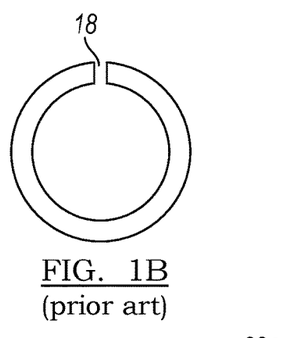
Figure 1C:
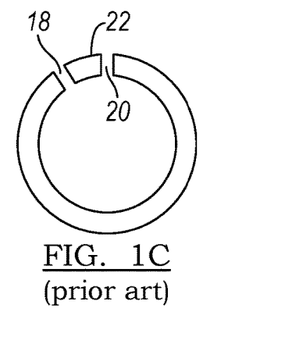

FIGS. 1A-1E are illustrative of a cutting scheme used to make a cutting tool by a known, prior art method. FIG. 1A shows an end view of a tube 10, such as a metal cannula, which has center 12. A cut is made starting along cut line 14 through the wall of the tube 10 at point 16, and continues longitudinally through a portion of the tube wall. The cut line 14 is coincident with a radius of tube 10 and therefore passing through the center 12. This results in cut 18, which is shown in FIG. 1B. The tube 10 is then rotated counterclockwise and a second, identical cut 20 is made, as shown in FIG. 1C, to yield arm 22. The process is repeated to yield as many arms as desired; generally, the entire central region, longitudinally, of the cannula is cut to form a plurality of arms with spaces in between, as will be described below.

Figure 1D:
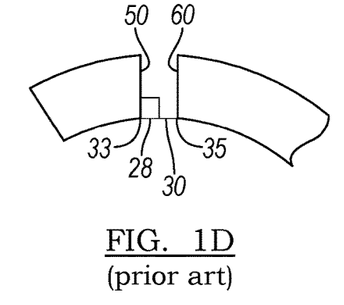
Figure 1E:
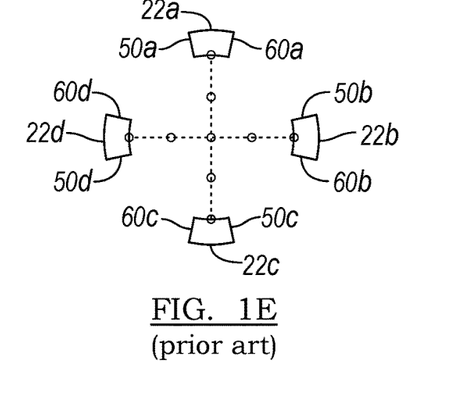

As shown in FIG. 1D, the cutting scheme described above and shown in FIGS. 1A-1C yields a cut which has an angle 28 the measure of which is approximately or exactly 90 degrees when taken with respect to a line 30, which is drawn between the innermost points of the edges of the cut (cut 18 is shown, but this explanation also applies to cut 20.) When an exemplary device comprising four arms 22a/22b/22c/22d is constructed in such fashion, as is shown in FIG. 1E, the result is the generation of four clockwise blades 60a/60b/60c/60d and four counterclockwise blades 50a/50b/50c/50d. Because all cuts have been made in the same fashion, all of the clockwise blades 60 and counterclockwise blades 50 have substantially the same sharpness, leading to a device that will cut uniformly regardless of whether the cutting element comprising the blades is rotated clockwise or counterclockwise.

In some cases, a device of this construction is suitable for the processing and treatment of an intravascular structure, such as an atherosclerotic plaque or a thrombus. However, because the face of the blade presented to the lesion during the removal process is a substantially flat face without a pronounced point, treatment may be limited in some cases to simple maceration of material rather than clean cutting. This may make removal of hardened material difficult or impossible, and may lengthen the treatment procedure.

Figure 2:
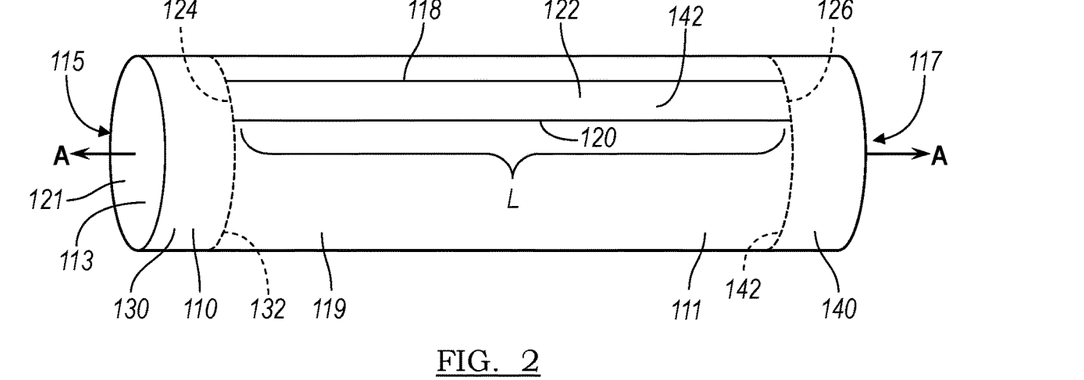
FIG. 2 is a perspective view of a series of cuts in a precursor tube made in accordance with an embodiment of the present disclosure.

A device 110, which is a cutting element for a rotary tool, is constructed in accordance with the principles of the present disclosure is illustrated in FIG. 2. Tube 111 has an outer surface 119 and inner surface 121, with a lumen 113 formed therethrough. The tube 111, and therefore the device 110, defines a longitudinal axis A, about which it is disposed. The device 110 extends from a first end 115 to a second end 117. The device 110 may further be subdivided into a first tubular portion 130, a second tubular portion 140, and a plurality of arms 122 attached to first tubular portion 130 and second tubular portion 140 and positioned therebetween.

The arms 122 are preferably of identical length L, which is defined by the distance between the first end 124 of the arm and the second end 126 of the arm 122. As shown in FIG. 2, the length L of the arms of the tube 111 is at what can be considered a longest length, wherein the tube 111 is substantially wholly cylindrical, and the arms 122 have not been bowed out radially away from the longitudinal axis A.

The length L of each arm 122 is preferably equal to the length L of every other arm 122 in order to provide a device 110 in which the arms 122 can be bent out of the device 110 to their final configuration in order to provide a consistent radius of curvature for the arms at their functional, cutting portions. The first ends 124 of the arms 122, in such an embodiment, align circumferentially at boundary 132, which along with first end 115 of the device 110, bound the first tubular portion 130 of the device 110. Likewise, the second ends 126 of the arms 122 align along at boundary 142 around the circumference of the tube 111, and along with second end 117 of tube 111 (and device 110) provide the bounds of the second tubular portion 140.

The arms 122 are provided by making two cuts through the outer surface 119 of the tube 111 and extending through the inner surface 121 of the tube 111, in this case first cut 118 and second cut 120. Preferably, a plurality of cuts are made at consistent intervals about the circumference of the device 110 such that the entire middle portion of the device (that is, the portion between first tubular portion 130 and second tubular portion 140) is made of a plurality of arms 122 with substantially the same characteristics as one another.

Figure 3A:
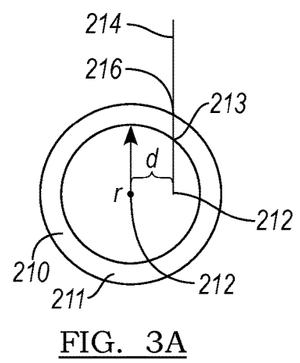
FIGS. 3A-3E are schematic views of cuts made to create a vascular treatment device constructed in accordance with an embodiment of the present disclosure.
Figure 3B:
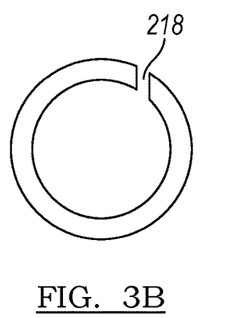
Figure 3C:
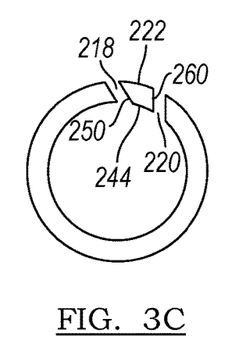

Turning to FIG. 3A, one example of a way of making the plurality of cuts in order to generate a plurality of arms for a device is illustrated. A device 210 is made by cutting tube 211 off-center. The tube 211 has a center 212, and a laser 214 (or other cutting too) is used to make a cut parallel to the radius r of the tube 211, a distance d away from said radius r. The resultant cut 218 may be seen in FIG. 3B. The cut 218 passes through the outer surface 216 of the tube and to the inner surface 213 of the tube 211, giving rise to the first cut 218. The tube is then rotated as shown in FIG. 3C and a similar second cut 220 is made, thus creating arm 222 out of the material of tube 211.

Figure 3D:
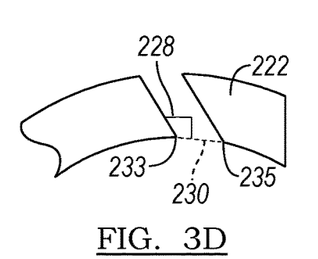
Figure 3E:
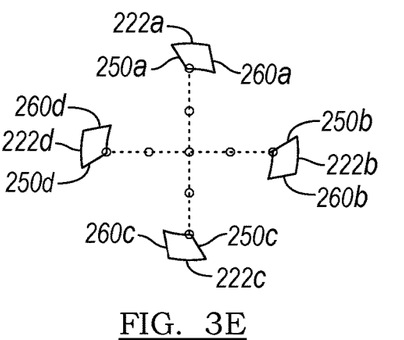

As can be seen in FIGS. 3D and 3E, the result of making such an off-center cut is the generation of an arm 222 that has two different types of blades 250 and 260 with varying sharpness. The off-center cut leads to a pair of angles 228 and 232 which, when measured relative to a straight line 230 drawn between the corners of the cut along the inner surface 213 of the tube, do not have the same measure. As illustrated, angle 228 is obtuse, and angle 232 is acute. The cut 220, made in the same way, ensures that the next arm will have similar properties. The blade 250, in which the obtuse angle is internal to the arm 222, will be a sharper blade than blade 260, in which the acute angle is internal to the arm 222. By making such cuts about the entire circumference of the tube 211 at consistent distances thereabout, a plurality of arms 222 with sharp blades 250a, 250b, 250c, 250d and duller blades 260a, 260b, 260c, and 260d will be generated. As illustrated, the sharper blades will be the tissue-contacting blades when the device is rotated counterclockwise, and the duller blades will contact the tissue when the device is rotated clockwise.

Figure 4A:
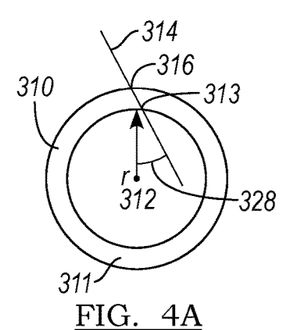
FIGS. 4A-4E are schematic views of cuts made to create a vascular treatment device constructed in accordance with a further embodiment of the present disclosure.
Figure 4B:
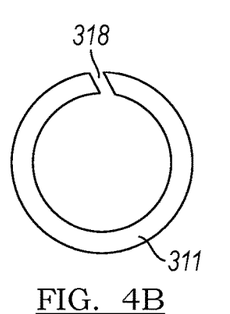
Figure 4C:
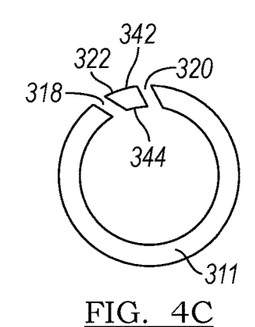

FIGS. 4A-4E illustrate a different method of making a device 310 according to the principles of the present disclosure. Rather than making cuts through the tube 311 parallel to a radius r as in FIG. 3, the device 310 of FIG. 4 is made by making a cut along cut line 314 through a point 316 on the outer surface and a second point 313 on the inner surface of the tube 311. The cut line 314 forms an angle 328 between the radius r which would, if continued, extend through the contact point 316, which does not have a measure of 0 degrees, or 90 degrees, or 180 degrees. Such a cut line 314 may be contained in a plane which is out-of-plane with the longitudinal axis A in some embodiments. The first cut 318 can be seen in FIG. 4B. A second cut 320 is made, circumferentially displaced from the first cut 318, and defining arm 322 therebetween, as shown in FIG. 4C.

Figure 4D:
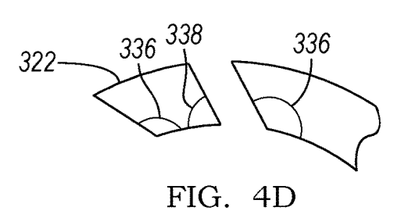
Figure 4E:
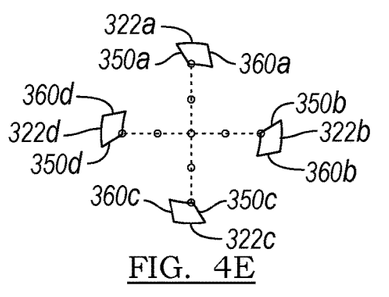

As illustrated in FIG. 4D, the cut 318 (or 320) defines a pair of angles 338 and 336 internal to the arm 322 on either side of the cut. For the purposes of illustration, first angle 336 is an obtuse angle, and second angle 338 is an acute angle. Thus, the side of the arm 322 containing the obtuse first angle 336 forms a sharp blade 350 and the side of the arm 322 containing the acute second angle 338 defines a dull blade 360. The blades of a four-armed device are illustrated in FIG. 4E.

Figure 5:
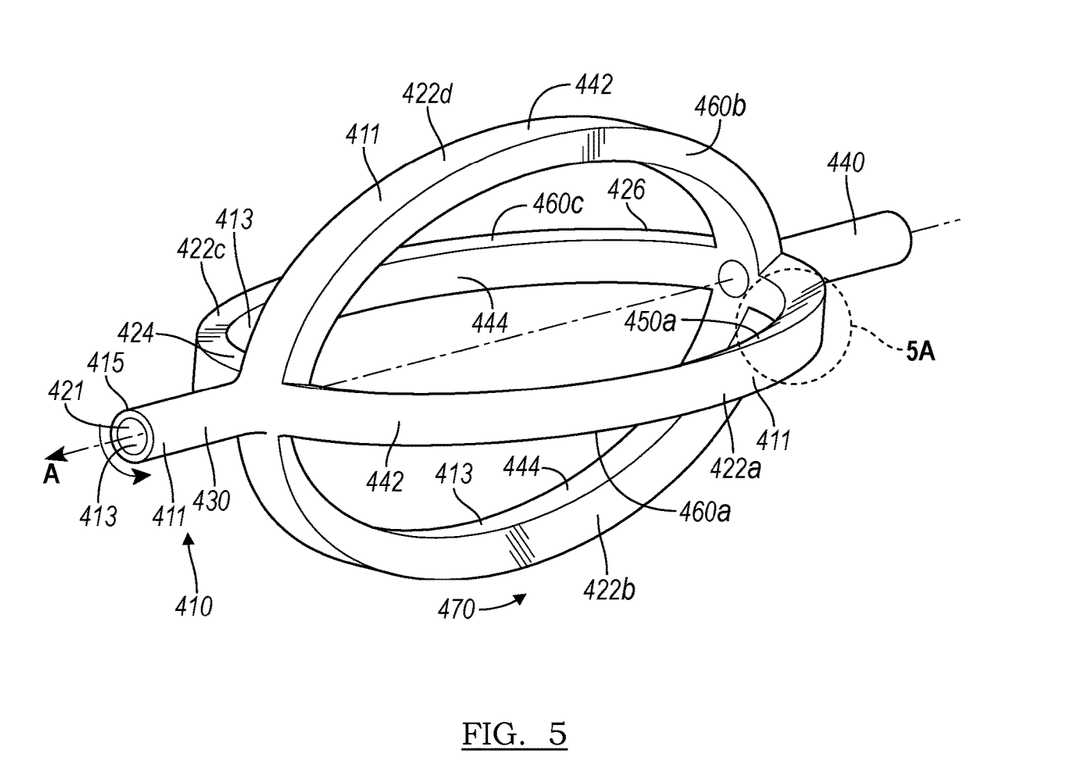
FIG. 5 is a perspective view of a device constructed in accordance with an embodiment of the present disclosure.

FIG. 5 is a depiction of a device 410 in accordance with the principles of the present disclosure shown in an expanded state, as it would be deployed to the lumen of a body vessel for use. In the expanded state, the arms 422a/b/c/d are extended radially away from the longitudinal axis A defined through the tube 411 (or the device 410). The device 410 can be said to have the shape of a malecot device. The device 410 extends from first end 415 to second end 417. The plurality of arms 422 are attached to, and disposed between, first tubular portion 430 and second tubular portion 440, and define a plurality of relatively sharp blades 450 and relatively dull blades 460. When the device 410 is rotated in a counterclockwise direction 470, the sharp blades 450 engage the obstruction or material to be treated; when rotated in clockwise direction 480, the duller blades 460 are instead the working surface of the device 410, and engage the obstruction to be removed.

Figure 5A:
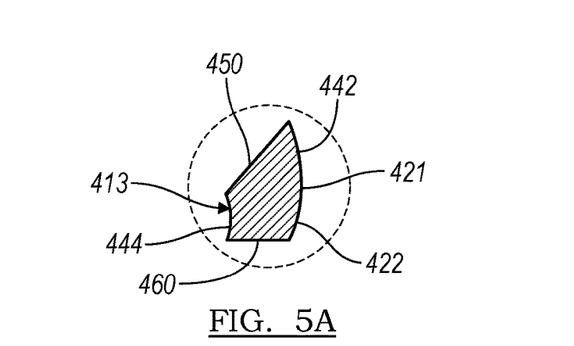
FIG. 5A is a close up view of a blade profile of the device of FIG. 5.

FIG. 5A shows a cross-sectional view of an arm 422 of the device 410 of FIG. 5. Arm 422 has an inner surface 413 and an outer surface 421, with edges 442 and 444 bounding the sides of the arm 422 in a radial dimension. The edge 442 doubles as blade 450, and the edge 444 doubles as blade 460. A device constructed in accordance with the principles of the disclosed embodiments has blades that are formed in a radial dimension, in that they proceed from the outer surface 421 to the inner surface 413, and in doing so, the distance from the center of the tube 411 is decreased. The arms 422 of the present disclosure are also, in a collapsed configuration of the device 410 (wherein the arms 422 are compressed into the tube 411 so as to form a cohesive, cylindrical outer surface 413 of said tube), in some embodiments made substantially parallel to the longitudinal axis A. In other embodiments, the arms may be differently constructed, but are non-helical elements of the device.

The precursor tube of any embodiment of the present disclosure may be made of any suitable material. For embodiments in which tissue is to be excised or macerated, one suitable material may comprise a metal which is biocompatible. In some cases, the metal may be an alloy such as surgical stainless steel or the like. In other embodiments, the metal may be a shape memory metal. A shape memory metal may be advantageously employed in order to facilitate a transition from an expanded state (with blades exposed) to a contracted or collapsed state (with blades pulled radially even with the remainder of the tube). Examples of shape memory metals include, but are not limited to, nickel/titanium alloys, cobalt/chromium alloys, and nickel/chromium alloys.

The device illustrated in FIG. 5 shows a device 410 having four arms 422a/422b/422c/422d. It will be appreciated that a device with any number of arms, including three, five, six, eight, ten, twelve, and so forth, may be made without departing from the spirit of the present disclosure. It will be understood by a person of ordinary skill in the art that any of the blade cutting schemes disclosed herein could be used to make such a device.

In some embodiments, based for example on the device 410 illustrated in FIG. 5, the arms 422a/b/c/d may have different characteristics from one another. For instance, the arm 422a may bear a sharper blade than does arm 422b. In one example, the arm 422c may have a similar blade sharpness to that of 422a, and arm 422b may have a similar blade sharpness to arm 422d, such that when the device 410 is rotated, a sharp blade encounters the thrombus, then a dull blade, then a sharp blade in alternating fashion. The number of arms and sharpness characteristics of such arms may be tailored to the type of thrombus the device is expected to encounter.

Figures 6A, 6B:
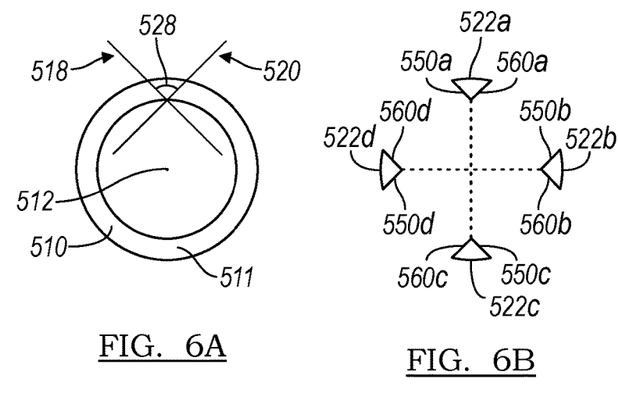
FIGS. 6A-6C are schematic views of blade profiles of further embodiments of the present disclosure.
Figure 6C:
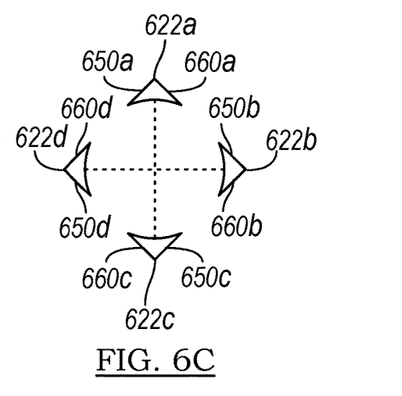

Further embodiments of methods of cutting a tube or cannula to yield a cutting device are shown in FIGS. 6A-6C. Like the blade-bearing arms of embodiments described previously, the arms 522 and 622 as shown in FIGS. 6B and 6C are created by making two cuts through the outer and inner surfaces of the tube. Contrary to previous embodiments, however, the cut lines 518 and 520 intersect at the inner surface 513 of the tube 511, thereby causing the bottom surface of the arm 522 to effectively be a single straight line. The cut lines 518 and 520 intersect to form an angle 528. The cut lines 518 and 520 may approach the tube 511 from different angles, leading to a different sharpness of the blade 550a/b/c/d from that of blade 560a/b/c/d. Similarly, the cut lines that form the arms 622a/b/c/d of the device of FIG. 6C intersect, but at the outer surface 621 of the tube 611 rather than at the inner surface.

Figure 7:
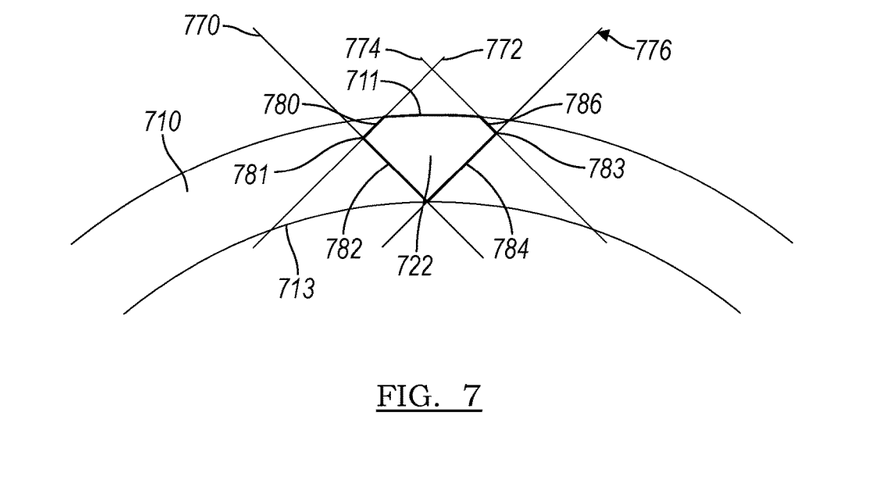
FIG. 7 is a schematic view of blades cut for a device in accordance with the principles of another embodiment of the present disclosure.

FIG. 7 illustrates a further embodiment of the device constructed in accordance with the principles of the present disclosure. In this case, four cuts 772/774/770/776, rather than two, are made in the tube 711 to yield arm 722, which has blade 781 located at the intersection of cuts 770 and 772, and blade 783 located at the intersection of cuts 774 and 776. Blade 781 is a leading edge located between faces 780 and 782, and blade 783 is a leading edge located between faces 784 and 786, respectively, on opposite sides circumferentially of faceted blade arm 722. The blades 781/783 are located radially inward relative to the outer surface 713 of the tube 711, thereby allowing a first point of contact with the tissue to be cut which in turn is positioned inward relative to the wall of the vessel in which the rotary blade is to be introduced. Each of cuts 770/772/774/776 may be made at a different angle relative to the outer surface 713 of tube 711, allowing for blades 781/783 to be located at different positions relative to the center of the device 710, and to have differing sharpness.

Figure 8:
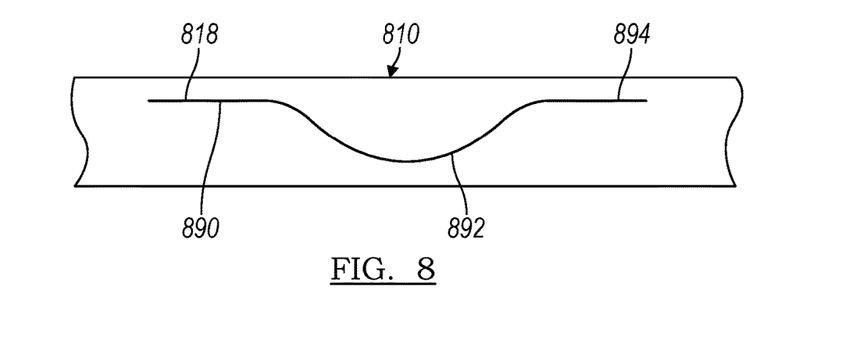
FIG. 8 is a side view of a cut made in a tube when constructing a device in accordance with another embodiment of the device disclosed herein.

In another embodiment, the cuts made in the tube need not be linear, and can give rise to an alternatively-shaped blade. As shown in FIG. 8, a non-linear cut 818 is made in tube 811. The profile of the cut is such that it contains a substantially linear portion 890, an arc 892, and a second substantially linear portion 894. When parallel cuts are made along the circumference of tube 811, the result is a bladed device 810 which has similarly-shaped arms that are effective to cut and macerate tissue similar to other embodiments of the device as disclosed herein.

In addition to making non-linear cuts 818 through the surface of a tube 811, the incident angle of the laser may be changed in this embodiment along the length of the non-linear cut 818. This allows for regions of greater or less sharpness along the length of the arm 822. In another embodiment, the incident angle may be held constant at a first angle for the first cut that forms the arm 822, and held constant at a second angle for the second cut, in order to generate two blades with differing sharpness on the same arm 822.

Figures 9A, 9B:
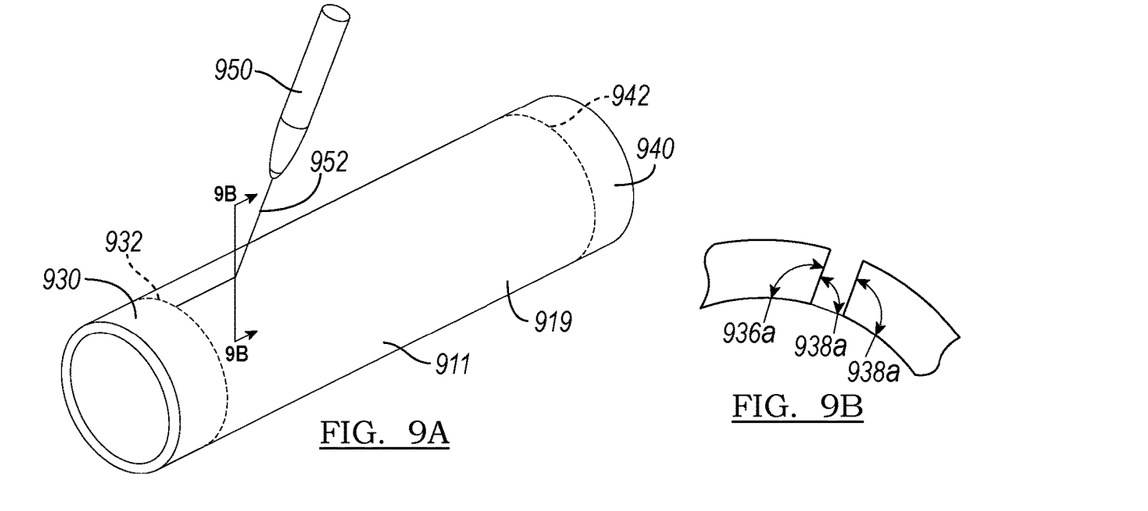
FIGS. 9A-9E are views of a cutting scheme and blades in accordance with another aspect of the present disclosure.
Figures 9C, 9D:
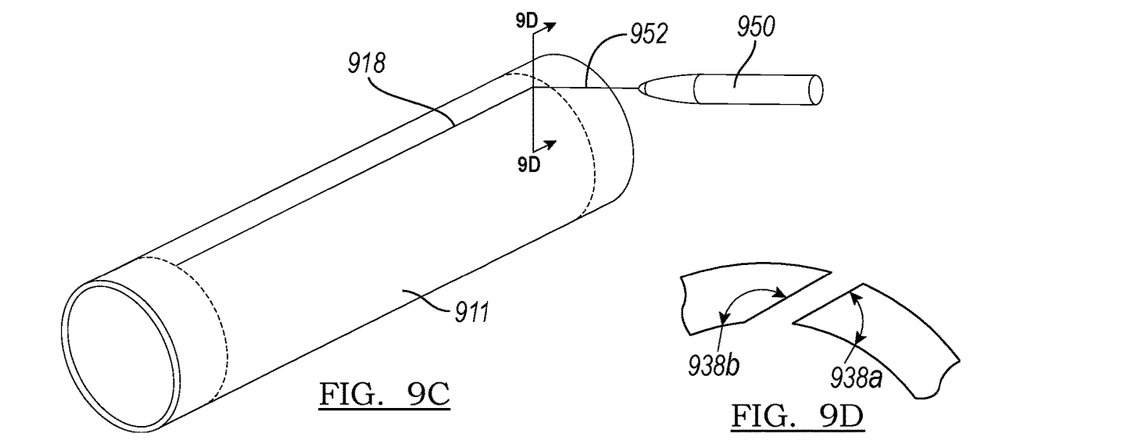

In another embodiment, as illustrated in FIGS. 9A-9E, a tubular body 911 may be cut by a laser 950 using a method that results in areas of varying sharpness along an edge of the resultant arm 922. In this embodiment, the laser cut may be a substantially straight (that is, parallel to the longitudinal axis which runs through the tubular body 911) as it originates at boundary 932 and passes through the outer surface 919 of the tubular body 911. However, the angle of approach of the laser 950 may be altered long the length of the cut 918, thus resulting in a plurality of zones of varying sharpness. As shown in FIG. 9A, the beam 952 of laser 950 cuts the tubular body 911 at a first angle, resulting in a cut as shown in FIG. 9B with first acute angle 936a and first obtuse angle 938a. The laser may then be rotated about the tubular body 911 as the cut 918 advances toward boundary 942 at a second angle as shown in FIG. 9C, resulting in a portion of the arm 922 shown in FIG. 9D having an acute angle 936b having a different measure from the acute angle 936a, and a corresponding obtuse angle 938b having a different measure from angle 938a. In another embodiment, the cut 918 may result in a blade portion having a right angle portion.

Figure 9E:
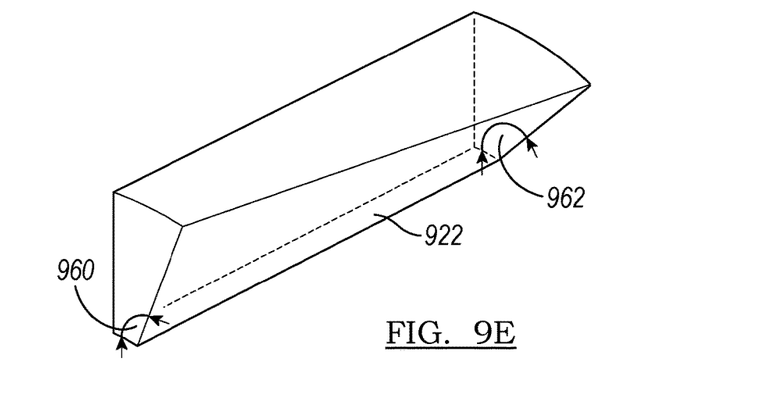

An example of an arm 922 resulting from a cutting regimen as described above is shown in isolation in FIG. 9E. At first end 924, the blade of arm 922 makes a first inner angle 960, and at second end 926, the blade has a second inner angle 962 different from first inner angle 960. In some embodiments, the inner angle along the blade may change multiple times. In other embodiments, the center of the arm 922, where the diameter is greatest and there is a chance of contacting the vessel wall, may be constructed as a back bevel in order to minimize trauma.

A cutting device with arms 922 having a variety of blade regions of varying sharpness. Such a structure may be suitable for excising a heterogeneous thrombus, which may have firm portions, gel-like and liquid portions, and may be best treated by exposure to a cutting tool having a variety of regions of sharpness.

A cutting device of the present disclosure may be operably attached to a rotary tool, preferably one which includes a motor capable of rotating the bladed device in both a clockwise and a counterclockwise direction. The rotary tool may be coupled to a handle which allows a user to manipulate the device once it has been delivered to an intravascular site to be treated. The handle may include means of modulating the mode of operation of the device, such as a thumbswitch. The thumbswitch is able to change the device from an off condition, to one in which rotation in the clockwise direction is facilitated, to one in which rotation in the counterclockwise direction is facilitated. The assembly may also include a delivery sheath which contains the cutting portion of the device. When the cutting portion is inside the delivery sheath, it takes on its collapsed position. When it is pushed out of the sheath, or the sheath is retracted proximally toward the practitioner, the arms adopt their radially expanded configuration, thereby enabling rotational cutting and/or maceration of tissue.

As a person skilled in the art will readily appreciate, the above description is only meant as an illustration of implementation of the principles this application. This description is not intended to limit the scope of this application in that the system is susceptible to modification, variation and change, without departing from the spirit of this application, as defined in the following claims.

What is claimed is:

1. A medical device for disrupting material in a body vessel, the medical device comprising:
    a body comprising a first end and extending to a second end, the body comprising an inner surface and an outer surface opposite the inner surface and defining a longitudinal axis therethrough, the body comprising a first tubular portion comprising the first end, a plurality of arms, and a second tubular portion comprising the second end and being axially displaced from the first tubular portion, the plurality of arms being disposed between and connected to the first tubular portion and the second tubular portion,
    each of the plurality of arms being formed longitudinally and comprising:
        an outer face continuous with the outer surface,
        an inner face continuous with the inner surface,
        a first blade, and
        a second blade opposite the first blade;
        each of the first blade and the second blade being disposed between the outer face and the inner face, the first blade being sharper than the second blade; and
        each of the plurality of arms being arranged such that each first blade is in a same relative orientation in a circumferential direction.

2. The medical device of claim 1, wherein the body comprises a malecot.

3. The medical device of claim 1, wherein the body comprises metal.

4. The medical device of claim 3, wherein the metal comprises a nickel-titanium alloy.

5. A medical device for disrupting material in a body vessel, the medical device comprising:
    a body comprising a first end and extending to a second end, the body comprising an inner surface and an outer surface opposite the inner surface and defining a longitudinal axis therethrough, the body comprising a first tubular portion comprising the first end, a plurality of arms, and a second tubular portion comprising the second end and being axially displaced from the first tubular portion, the plurality of arms being disposed between and connected to the first tubular portion and the second tubular portion,
    each of the plurality of arms being formed longitudinally and comprising:
        an outer face continuous with the outer surface,
        an inner face continuous with the inner surface,
        a first blade, and
        a second blade opposite the first blade;
        each of the first blade and the second blade being disposed between the outer face and the inner face, the first blade being sharper than the second blade; and each of the plurality of arms being arranged such that each first blade is in a same relative orientation in a circumferential direction, and wherein the second blade is disposed at an angle relative to a cross-sectional diameter line of the device.

6. The medical device of claim 5, wherein the first blade has an obtuse angle internal to the arm, and the second blade has an acute angle internal to the arm.

7. The medical device of claim 5, wherein the body comprises a malecot.

8. The medical device of claim 5, wherein the body comprises metal.

9. The medical device of claim 8, wherein the metal comprises a nickel-titanium alloy.

10. A medical device for disrupting material in a body vessel, the medical device comprising:

a body comprising a first end and extending to a second end, the body comprising an inner surface and an outer surface opposite the inner surface and defining a longitudinal axis therethrough, the body comprising a first tubular portion comprising the first end, a plurality of arms, and a second tubular portion comprising the second end and being axially displaced from the first tubular portion, the plurality of arms being disposed between and connected to the first tubular portion and the second tubular portion, each of the plurality of arms being formed longitudinally and comprising:
an outer face continuous with the outer surface,
an inner face continuous with the inner surface,
a first blade, and
a second blade opposite the first blade;
each of the first blade and the second blade being disposed between the outer face and the inner face, the first blade being sharper than the second blade; and
each of the plurality of arms being arranged such that each first blade is in a same relative orientation in a circumferential direction, and wherein the plurality of arms are non-helical.

11. The medical device of claim 10, wherein the plurality of arms are parallel to the longitudinal axis between the first and second tubular portions.

12. The medical device of claim 10, wherein the body comprises a malecot.

13. The medical device of claim 10, wherein the body comprises metal.

14. The medical device of claim 13, wherein the metal comprises a nickel-titanium alloy.

* * * * *